United States Patent [19]

Miyata et al.

[11] 4,098,571
[45] Jul. 4, 1978

[54] SUBSTITUTE BLOOD VESSEL AND A PROCESS FOR PREPARING THE SAME

[75] Inventors: Kaneyasu Miyata, 93-2 Aza-Higashiyama, Oaza-Kamiyashiro, Idaka-cho, Meito-Ku, Nagoya City, Aichi Prefecture, Japan; Izumi Amano, No. 301, Murakami Bldg., 5-48 Yatomi-Dori, Mizuho-ku, Nagoya City, Aichi Prefecture, Japan; Takehiko Iwai, Osaka; Tetsuya Asahi, Toyonaka, both of Japan

[73] Assignees: Kaneyasu Miyata; Izumi Amano, both of Nagoya; Kohei Toda, Osaka, all of Japan

[21] Appl. No.: 711,599

[22] Filed: Aug. 4, 1976

[30] Foreign Application Priority Data

Sep. 2, 1975 [JP] Japan .................. 50-106626

[51] Int. Cl.² .......................... A61F 1/24

[52] U.S. Cl. .......................... 8/94.11; 3/1; 3/1.4

[58] Field of Search .......... 3/1, 1.4; 8/94.11

[56] References Cited

U.S. PATENT DOCUMENTS

2,900,644  8/1959  Rosenberg et al. .................. 3/1
3,927,422  12/1975  Sawyer .................................. 3/1

Primary Examiner—John Kight, III
Attorney, Agent, or Firm—Shlesinger, Arkwright, Garvey & Dinsmore

[57] ABSTRACT

A process for preparing a heterograft substitute blood vessel comprises digesting a properly pretreated pig blood vessel with a digesting solution containing an animal proteolytic enzyme so as to retain collagenous and elastic fiber constituents substantially in the original state and substantially remove away other tissue constituents of said blood vessel than said two kinds of constituents, and then fixing the resulting digested blood vessel into a desired shape with a liquid fixing agent.

10 Claims, 3 Drawing Figures

FIG. 1 Extension Percentage Relative To Chymotrypsin Concentration and Treating Time FIG. 2 Extension percentage relative to the kind of enzyme solution

FIG. 3

SUBSTITUTE BLOOD VESSEL AND A PROCESS FOR PREPARING THE SAME

The present invention relates to a heterograft substitute blood vessel, and especially such a substitute blood vessel obtained from a pig blood vessel and a process for preparing the same.

An excellent heterograft substitute blood vessel or an artificial blood vessel is earnestly desired in clinical fields e.g. in the field of artificial dialysis medical treatment.

When an AV shunt blood vessel is applied to a patient continuously for a long time in this medical treatment, thrombus, bleeding, infection and varicosity concur, resulting in the successive failure of obtaining sufficient blood flow and of inserting or extracting a needle for drawing or injecting blood, and thus requiring the implantation of the vein obtained from another portion of his own or from another persons's.

However, the implantation of autoplastic vein graft is limited and that from other person is questionable because of causing much defect in the donor. Therefore, an artificial blood vessel is earnestly desired which is free from thrombus, bleeding, infection or varicosity even after frequent insertions and extractions of a needle for drawing or injecting blood. But, a satisfactory artificial inner shunt blood vessel of synthetic fiber material or the like suitable for dialysis has not been achieved yet.

There are also similar difficulties in other clinical fields covering the treatment of blood vessel, of course. On the other hand, many kinds of heterografts for blood vessel have been proposed for the purpose of these medical treatments. Recently, a collagen tube is being subject to clinical applications, which is obtained by digesting a bovine blood vessel with a vegetable proteolytic enzyme such as ficin so that substantially only the collagen fiber constituent remains and then fixing the same by treatment with a fixing agent.

This collagen tube, however, is inferior in its elastic properties such as extensibility, expandability or the like to a raw blood vessel, resulting in difficulties in case of continued employment, application to bendable body portions such as a joint, and frequent needle insertion and extraction. Further, since substantially all tissue of the blood vessel except collagen fiber constituent has been removed away by digestion and the original structure of a raw blood vessel has been practically lost, the inner wall of the collagen tube is biochemically much damaged in comparison with that of a raw blood vessel, thus raising a new problem in respect of thrombus formation.

An object of the present invention is to provide a new heterograft substitute blood vessel which retains the tissue structure of the original blood vessel and has sufficiently lowered antigenicity, and a process for preparing the same.

Another object of the present invention is to provide a new tubular heterograft substitute blood vessel which has remarkably improved elastic properties in comparison with those of a raw blood vessel and a conventional collagen tube, and a process for preparing the same.

A further object of the present invention is to provide a new heterograft substitute blood vessel of remarkably reduced possibility of occurance of thrombus, aneurysms, varices, dehiscence or the like, and a process for manufacturing the same.

A further object of the present invention is to provide a new heterograft substitute blood vessel which can be formed of an easily available and inexpensive material, and be thus manufactured at a lower cost, and a process for preparing the same.

In order to achieve the abovementioned objects, the process according to the present invention can be briefly summarized as follows.

That is, the process comprises the steps of subjecting a pig blood vessel to required preliminary treatments such as the removal of blood and foreign substances, the exfoliation of fat and connective tissue, the ligature of branches or tears of the blood vessel, the defreezing treatment for protein denaturation and the like, digesting the pig blood vessel with an animal proteolytic enzyme so as to retain the collagenous and elastic fiber constituents substantially in the original state and substantially remove away other tissue constituents than the abovementioned two kinds of constituents, and then fixing the same into a desired shape with a suitable liquid fixing agent.

A heterograft substitute blood vessel thus obtained according to the present invention is characterized in comparison with the conventional collagen tube in that the original structure is substantially retained with not only collagenous but elastic fiber constituent being reinforcedly fixed. As described later with detailed data, by thus retaining, as the tissue constituents of a substitute blood vessel, not only elastic but collagenous fiber constituent in the original structure and reinforcedly fixing the same, the substitute blood vessel according to the present invention is made advantageous in that its elastic properties such as extensibility, expandability, tensile strength and the like are much improved, and that physiological troubles such as thrombus formation are fully overcome since the intima of the blood vessel is little subject to biochemical damages.

The inventors have found a surprising fact that in spite of substantially perfect retaining of elastic fiber constituent, a substitute blood vessel according to the present invention is of such a low antigenicity as to permit it to be applied to clinical purposes.

Consequently, the technical significance of the present invention lies in that by substantially perfectly retaining elastic fiber constituent and fixing the same together with collagenous fiber constituent, the substitute blood vessel has been remarkably improved in its strength and elastic properties even in comparison with a raw blood vessel, while as the result of retaining both of the collagenous and elastic fiber constituents which are the main constituents of the blood vessel tissue, the substitute blood vessel, after the fixing treatment, retains its basic structure i.e. the three layer structure comprising the intima, media and adventitia reinforcedly fixed in its original state, so that the features of a raw blood vessel is handed down in an improved state, and especially thrombus formation can be prevented similarly to the case of a raw blood vessel because of the intima being little subject to biochemical damages, and also the antigenicity is satisfactorily lowered. Thus, the abovementioned disadvantages of the prior arts are completely overcome.

The present invention will be described in more detail with reference to the appended drawings.

Proteolytic enzymes usable in the process according to the present invention are animal proteolytic enzymes such as pepsin, trypsin, chymotrypsin and the like, the usefulness in this art of which have been confirmed by the inventors for the first time.

A properly pretreated pig blood vessel is subject to digesting treatment with a treating liquid containing one or more kinds of these enzymes, optionally a thrombus dissolving agent e.g. urokinase, and an anticoagulating agent e.g. heparin-sodium until the abovementioned extent of digestion is achieved.

The inventors have found that since vegetable proteolytic enzymes such as ficin, papain and the like used in manufacturing a collagen tube according to the prior art acts nonselectively upon other protein constituents than collagenous protein to decompose the same to have lower molecular weight, they are not suitable for use in digesting treatment according to the present invention in which elastic fiber constituent has to be indispensably retained.

On the other hand, the abovementioned animal proteolytic enzymes act extremely moderately upon even elastic fiber constituent as well as collagenous fiber constituent. Therefore, it proved that these animal proteolytic enzymes have the characteristics of being easily adjustable with respect to its activity in the digesting treatment, and satisfactorily active upon muscular fiber constituent and structureless material inside and outside the cell, thus being very preferable to be used in the method according to the present invention.

In the conventional method for preparing a collagen tube from a bovine blood vessel, only vegetable proteolytic enzymes such as ficin, papain and the like are used as effective, and therefore there are inevitable difficulties in controlling the selective decomposition of the blood vessel tissue constituents. As a result of this and according to the common recognition in the technical field that other constituents of the blood vessel tissue than collagenous fiber constituent is unsuitable for the constituents of a substitute blood vessel in respect of their antigenicity, the development of a substitute blood vessel including elastic fiber constituent as a main component is unexpected from the viewpoint of the conventional art.

The inventor's knowledge that in respect of the activity upon the tissue protein constituent of a pig blood vessel, animal proteolytic enzymes are much more selective than vegetable ones is beyond the conventional common recognition in the art, and therefore the use of animal proteolytic enzyme in digesting treatment of a pig blood vessel is one of the important subject matters of the present invention.

For this purpose, one or more kinds of animal proteolytic enzymes are used, it may be preferable in respect of the control of the digesting treatment that two or more kinds of proteolytic enzymes of different substratespecificities are used in mixture.

Further, the digesting treatment with enzymes are more facilitated by using a freeze preserved pig blood vessel or other protein-denaturated pig blood vessel as the raw material.

The enzyme concentration of the digesting solution and the digestion time depend upon the kind of the enzyme and the condition of the blood vessel (denaturated, undenaturated or the like). Preferable examples of the combination of the concentration with the treating time are: with 100U/ml chymotrypsin liquid for 3 – 5 hours; with about 1% trypsin liquid for 3 – 5 hours; and with 0.5 – 2% pepsin liquid for 3 – 8 hours, in these cases the temperature being generally 30° – 40° C and at pH 1.8 – 9.0.

Further, the control of the requirements in the digesting treatment can be easily confirmed and achieved by the belowmentioned elasticity and histological tests.

Further, the fixing treatment with a liquid fixing agent may comprise any one of methods known in the process for preparing a bovine collagen tube (tanning methods), one example of which is a treatment with 5 – 10% formalin solution or 2 – 25% glutaric aldehyde for 2 – 4 weeks.

Into a blood vessel after the degesting treatment, a linear, T-, Y-, U-, or other shaped glass stylet is inserted to provide the blood vessel with a required shape.

Additional conditions for the said preliminary treatment to be noted in carrying out the process according to the present invention are now described. As abovementioned, one feature of a heterograft substitute blood vessel according to the present invention lies in its substantially perfect retention of the tissue structure of a raw blood vessel and thus the functions of the three layers thereof. To achieve this purpose by more satisfactorily retaining the functions of the three layers comprising the smooth intima rather free from thrombus formation, the media contributing to the extensibility and expandability of the blood vessel, and the adventita reinforcing the blood vessel with its strength requiredly kept, attentions have to be paid to the performance of 1 sufficiently washing the blood vessel immediately after the picking thereof to remove away blood and foreign substances on its inner wall without doing any mechanical damage thereto, and 2 removing, without damage to the adventitia, the surrounding tissue from the adventitia which is extended to the tissue and combined therewith.

By such a method according to the present invention as abovementioned, a new heterograft substitute blood vessel which is extremely elastic and has the main structure and functions of the raw blood vessel retained in an improved state. In addition, the substitute blood vessel according to the present invention is remarkably advantageous from the clinical and commercial viewpoints because of the easy availability of the required raw material.

The present invention will be described in more detail with reference to the following examples.

EXAMPLE

A fresh pig carotid artery was picked immediately following carcass splitting operation, put into a physiological salt solution containing 10,000 units/l of heparin sodium and carried home in an ice box. Immediately, the artery was freed of blood and foreign substances as completely as possible. Then, a glass stylet of a required diameter was inserted into the blood vessel, and fat and connective tissue were mechanically removed away from the adventitia.

After removing the stylet, the blood vessel was treated with various kinds of animal proteolytic enzymes of different substratespecificities a thrombus dissolving agent and an anticoagulating agent separately or in the form of a mixed solution (at pH 1.8 – 9.0, the temperature of 30° – 40° C and for 2 – 8 hours), and repeatedly washed by shaking the same in a physiological salt solution to inactivate and remove the enzymes. A glass stylet (linear, U-, or ω-shaped) was inserted again into the blood vessel, and fixed with 5 – 10% formalin (about 1.8 – 3.7% aqueous solution of formaldehyde) or 2 – 25% glutaric aldehyde solution for 2 – 4 weeks (the glass stylet being pulled out after 1 week's fixing treatment).

After the fixing treatment, the blood vessel was repeatedly washed by shaking in a physiological salt solution to remove the fixing agent, and then sterilized with 0.5% propiolactone solution. Then, the blood vessel was freed of the sterilizing agent by shake-washing in a physiological salt solution under the condition of aseptic manipulation, and preserved in 50% aquous solution of Japanese Pharmacopoeial ethanol.

Leakage and strength tests were performed on the product. One end of the blood vessel was connected to a pressurized air supply source with the other end bound up. Then the blood vessel was wholly sunk into water and the air pressure was raised for examining leakage. On the other hand, tensile test was performed by means of an autograph.

A product was regarded as successful which showed no air leakage at the air pressure of at least 250 mm Hg and showed more than 40% extensibility under 200 g load as well as more than 1.0 kg tensile strength.

According to the abovementioned general method, each kind of enzyme and ficin as a reference were treated under the following conditions.

1. Treatment with chymotrypsin:

Sections of fresh pig carotid artery freed from fat and connective tissue on the adventitia were put into 20 ml per 1 g of wet blood vessel of 0.1 M buffering boric acid solutions at pH 7.6 containing 5 mili M calcium chloride, 12 I.U./ml of urokinase, 10 units/ml of heparin, 10, 50, or 100 units/ml of chymotrypsin, and treated at 37° C for a time up to 5 hours. One sample of the blood vessel was taken out every one hour, and manufactured to a product according to the abovementioned process. Fixing treatment was performed with 5% formalin solution at 27° C for 2 weeks, where extensibility and others were measured every one hour.

2. Treatment with trypsin

Sections of fresh pig carotid artery freed from fat and connective tissue on the adventitia were treated in 20 ml per 1 g of wet blood vessel of 0.1 M buffering phosphate liquid at pH 7.55 containing 0.01, 0.1 or 1% of tripsin at 37° C for 5 hours. The extension percentage or others were measured every one hour.

3. Treatment with ficin(Reference):

Sections of fresh pig carotid artery freed from fat and connective tissue on the adventitia coat were treated in 20 ml per 1 g of wet blood vessel of McIlvaine buffer liquid at pH 5.5 containing 1 mg/ml of cystein hydrochloride and 10 mg/ml of ficin at 37° C for 5 hours. According to the process of Example 1, products were obtained. The extension percentage and others were measured every one hour.

Though all of the raw material used in the abovementioned examples were raw pig blood vessels, a freeze-preserved blood vessel, or other protein denatured blood vessel can also be digested by a similar process. Further, a single enzyme system was used here for the purpose of comparison, but with mixed enzyme systems, other advantages can be achieved as abovementioned.

EXTENSIBILITY TEST [1]

(1) Extensibility and load resistance were measured on each of kinds of specimens obtained in the abovementioned Examples, specimens treated with ficin as references, sections of raw pig carotid artery (A), products obtained by the fixing treatment of the said pig carotid artery (B), and commercially available bovine collagen tube (Bovine manufactured by Johnson & Johnson Co., Ltd.).

Method of test:
Apparatus Autograph S-100 (by Shimazu Manufacturing Co., Ltd.)

| Conditions weight | 500 g – 5000 g |
|---|---|
| length of specimen | 50 mm |
| tensile rate | 50mm/min. |
| recording rate | 50mm/min. |
| temperature | 25 – 26° C |
| moisture | 55 – 60% (relative moisture) |

The specimens in water-containing state were measured in the longitudinal direction of the cylindrical shape.

Figure 1:
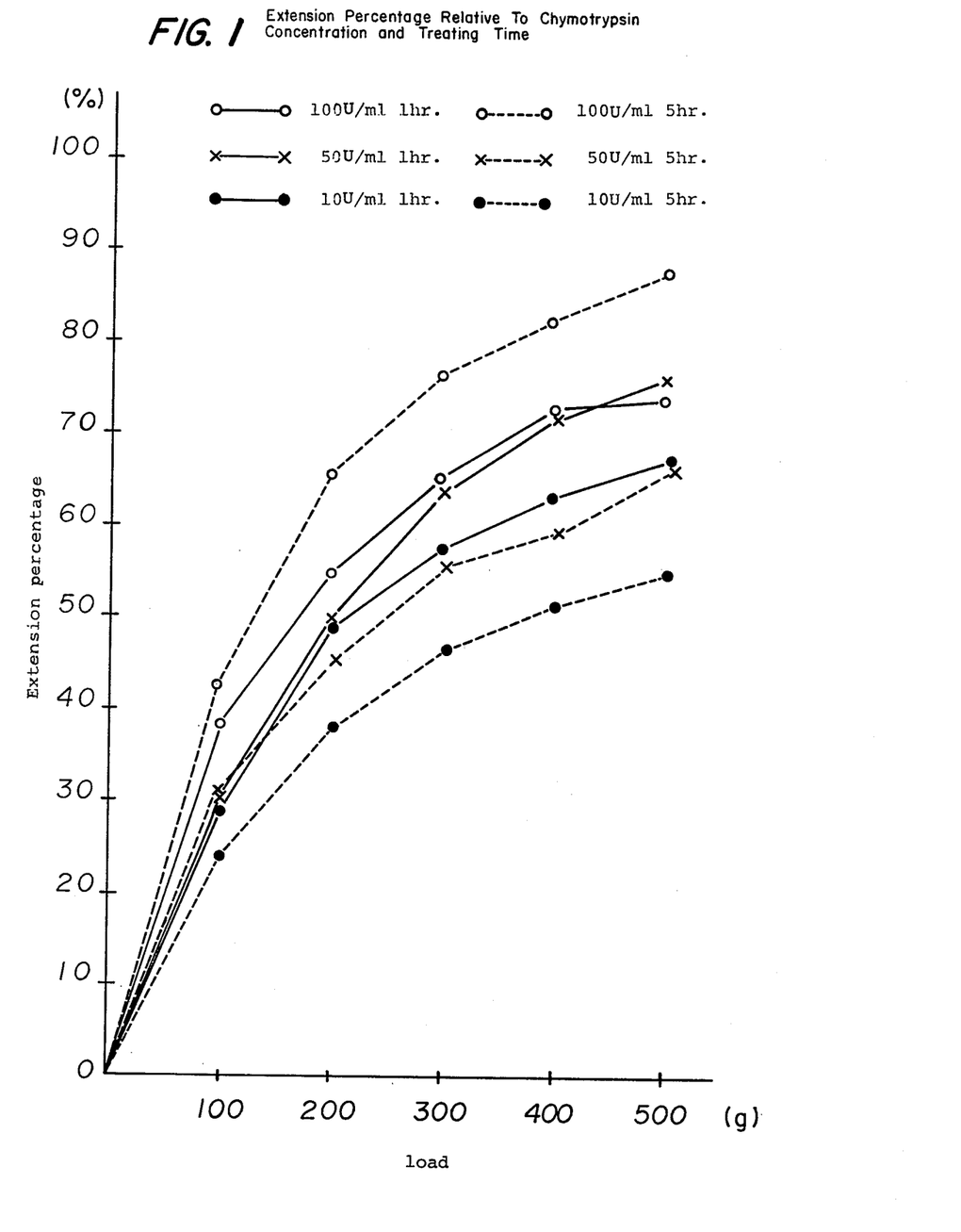
FIG. 1 is a graph illustrating the relation between the concentration of chymotrypsin, the treating time and the extensibility of a substitute blood vessel according to the process of the present invention.

In Tables 1 – 4 below and FIG. 1 in the appended drawings, the summerized result of this test is shown in which each value is the mean one of 5 specimens.

Table 1

| Treatment | Circumference (cm) | Thickness (mm) | Reference Extensibility(ΔL/L) × 100(%) | | | | | When Cut | |
|---|---|---|---|---|---|---|---|---|---|
| | | | 100 (g) | 200 (g) | 300 (g) | 400 (g) | 500 (g) | Load (kg) | Extensibility % |
| A | 1.45 | 0.64 | 30.0 | 39.6 | 45.0 | 48.2 | 51.1 | 2.91 | 94.2 |
| B | 1.30 | 0.46 | 20.6 | 35.8 | 48.2 | 57.2 | 62.8 | 2.58 | 92.4 |

Table 2

| 2 – 1 Treating Time | Treatment with chymotrypsin 100 U/ml Circumference (cm) | Thickness (mm) | Extensibility(ΔL/L) × 100(%) | | | | | When Cut | |
|---|---|---|---|---|---|---|---|---|---|
| | | | 100 (g) | 200 (g) | 300 (g) | 400 (g) | 500 (g) | Load (kg) | Extensibility % |
| 1 | 1.22 | 0.54 | 37.8 | 55.0 | 65.4 | 72.4 | 73.6 | 2.76 | 96.0 |
| 2 | 1.21 | 0.53 | 34.2 | 52.0 | 65.8 | 72.2 | 82.8 | 3.05 | 112.2 |

Table 2-continued
Treatment with chymotrypsin

2-1 100 U/ml

| Treating Time | Circumference (cm) | Thickness (mm) | Extensibility(ΔL/L) × 100(%) | | | | | When Cut | |
|---|---|---|---|---|---|---|---|---|---|
| | | | 100 (g) | 200 (g) | 300 (g) | 400 (g) | 500 (g) | Load (kg) | Extensibility % |
| 3 | 1.33 | 0.59 | 33.4 | 55.4 | 66.4 | 72.8 | 76.8 | 2.31 | 114.2 |
| 4 | 1.13 | 0.51 | 31.8 | 49.0 | 57.6 | 62.0 | 66.2 | 1.73 | 87.8 |
| 5 | 1.24 | 0.57 | 42.2 | 65.2 | 76.0 | 82.2 | 86.8 | 1.86 | 114.6 |

2-2 50 U/ml

| Treating time | Circumference (cm) | Thickness (mm) | Extensibility(ΔL/L) × 100(%) | | | | | When Cut | |
|---|---|---|---|---|---|---|---|---|---|
| | | | 100 (g) | 200 (g) | 300 (g) | 400 (g) | 500 (g) | Load (kg) | Extensibility % |
| 1 | 1.24 | 0.47 | 30.2 | 50.0 | 64.6 | 72.0 | 76.2 | 1.78 | 98.8 |
| 2 | 1.20 | 0.50 | 36.0 | 53.6 | 63.0 | 69.0 | 72.4 | 1.90 | 92.2 |
| 3 | 1.10 | 0.50 | 38.2 | 57.6 | 66.2 | 74.8 | 78.8 | 2.16 | 107.2 |
| 4 | 1.28 | 0.48 | 31.8 | 66.0 | 78.2 | 84.4 | 86.4 | 2.52 | 125.0 |
| 5 | 1.26 | 0.50 | 30.6 | 45.0 | 55.4 | 59.0 | 65.8 | 1.81 | 85.8 |

2-3 10 U/ml

| Treating time | Circumference (cm) | Thickness (mm) | Extensibility(ΔL/L) × 100(%) | | | | | When Cut | |
|---|---|---|---|---|---|---|---|---|---|
| | | | 100 (g) | 200 (g) | 300 (g) | 400 (g) | 500 (g) | Load (kg) | Extensibility % |
| 1 | 1.38 | 0.50 | 29.2 | 49.0 | 57.4 | 63.2 | 66.8 | 2.33 | 97.6 |
| 2 | 1.24 | 0.51 | 28.6 | 47.0 | 56.8 | 62.0 | 66.0 | 2.38 | 96.8 |
| 3 | 1.32 | 0.54 | 38.4 | 58.8 | 69.6 | 74.4 | 78.0 | 1.70 | 103.8 |
| 4 | 1.27 | 0.52 | 31.8 | 50.0 | 59.0 | 63.4 | 66.8 | 1.46 | 83.6 |
| 5 | 1.23 | 0.49 | 23.8 | 37.6 | 46.0 | 51.0 | 54.6 | 2.72 | 83.2 |

Table 3
Treatment with trypsin

3-1 0.01%

| Treating time | Circumference (cm) | Thickness (mm) | Extensibility(ΔL/L) × 100(%) | | | | | When Cut | |
|---|---|---|---|---|---|---|---|---|---|
| | | | 100 (g) | 200 (g) | 300 (g) | 400 (g) | 500 (g) | Load (kg) | Extensibility % |
| 1 | 1.20 | 0.46 | 32.4 | 55.2 | 66.0 | 71.6 | 75.4 | 1.91 | 102.4 |
| 2 | 1.24 | 0.53 | 38.2 | 53.0 | 62.6 | 67.2 | 72.6 | 3.49 | 107.6 |
| 3 | 1.30 | 0.46 | 28.8 | 51.2 | 62.6 | 68.0 | 71.2 | 2.17 | 101.2 |
| 4 | 1.13 | 0.51 | 39.8 | 55.0 | 62.0 | 65.6 | 68.8 | 1.99 | 94.2 |
| 5 | 1.20 | 0.48 | 37.8 | 59.6 | 70.0 | 75.4 | 78.4 | 2.03 | 101.6 |

3-2 0.1%

| Treating time | Circumference (cm) | Thickness (mm) | Extensibility(ΔL/L) × 100(%) | | | | | When Cut | |
|---|---|---|---|---|---|---|---|---|---|
| | | | 100 (g) | 200 (g) | 300 (g) | 400 (g) | 500 (g) | Load (kg) | Extensibility % |
| 1 | 1.14 | 0.46 | 32.4 | 55.8 | 68.0 | 73.2 | 77.8 | 1.67 | 109.0 |
| 2 | 1.20 | 0.50 | 36.0 | 53.6 | 63.0 | 69.0 | 73.0 | 1.90 | 92.2 |
| 3 | 1.30 | 0.46 | 33.2 | 57.6 | 69.8 | 75.2 | 79.0 | 1.77 | 101.6 |
| 4 | 1.28 | 0.48 | 31.8 | 66.0 | 78.2 | 84.4 | 87.8 | 2.52 | 125.0 |
| 5 | 1.32 | 0.40 | 33.6 | 57.8 | 66.4 | 71.2 | 74.0 | 1.61 | 92.0 |

3-3 1.0%

| Treating time | Circumference (cm) | Thickness (mm) | Extensibility(ΔL/L) × 100(%) | | | | | When Cut | |
|---|---|---|---|---|---|---|---|---|---|
| | | | 100 (g) | 200 (g) | 300 (g) | 400 (g) | 500 (g) | Load (kg) | Extensibility % |
| 1 | 1.33 | 0.38 | 30.6 | 53.8 | 63.6 | 68.4 | 71.4 | 1.67 | 91.4 |
| 2 | 1.36 | 0.50 | 34.6 | 56.2 | 66.0 | 71.4 | 74.6 | 2.52 | 102.4 |
| 3 | 1.37 | 0.41 | 30.2 | 53.0 | 63.2 | 69.0 | 73.0 | 1.52 | 98.2 |
| 4 | 1.06 | 0.53 | 46.2 | 70.8 | 81.0 | 86.2 | 90.6 | 2.62 | 121.6 |
| 5 | 1.28 | 0.35 | 38.8 | 63.6 | 72.8 | 76.6 | 79.6 | 1.50 | 97.8 |

Table 4

| | Treatment with ficin (reference) | | | | | | | | |
|---|---|---|---|---|---|---|---|---|---|
| | 1% ficin | | | | | | | When Cut | |
| Treating time | Circumference (cm) | Thickness (mm) | Extensibility(ΔL/L) × 100(%) | | | | | Load (kg) | Extensibility % |
| | | | 100 (g) | 200 (g) | 300 (g) | 400 (g) | 500 (g) | | |
| 1 | 1.25 | 0.36 | 23.0 | 37.6 | 49.4 | 57.0 | 62.4 | 2.16 | 99.2 |
| 2 | 1.26 | 0.23 | 24.6 | 38.6 | 45.0 | 49.2 | 52.0 | 2.00 | 78.0 |
| 3 | 1.53 | 0.11 | 10.2 | 14.4 | 17.6 | 19.8 | 21.6 | 1.77 | 38.8 |
| 4 | 1.51 | 0.13 | 6.3 | 9.3 | 12.0 | 14.0 | 16.0 | 1.18 | 29.0 |
| 5 | 1.49 | 0.11 | 3.4 | 4.6 | 5.4 | 6.7 | 7.6 | 1.63 | 15.6 |
| Bovine | 2.30 | 0.50 | 1.6 | 2.0 | 2.6 | 3.2 | 4.0 | — | — |

It has proved from these results that in case of the treatment with 10 U/ml chymotrypsin all specimens but one treated for 5 hours showed more than 40% of extension percentage at 200 g load, thus having an elasticity similar to or higher than that of the raw blood vessel. Further, in case of the treatment with trypsin, all products thus obtained came up to the abovementioned standard.

On the other hand, in case of the treatment with 1% ficin as the reference, the one hour-treated specimens showed an extension percentage similar to that of the raw blood vessel at 200 g load, two hour-treated specimens showing one similar to or slightly lower than that of the raw blood vessel, while such an extension percentage suddenly dropped after 3 hour-treatment, being only 15% at 200 g load then, and about 5% after 5 hour-treatment showing little elasticity.

Extension Test [II]

Activity of each enzyme was tested using casein as substrate. The result is that 1% ficin, 1% trypsin and 100 U/ml chymotripsin solutions showed similar activity respectively.

Figure 2:
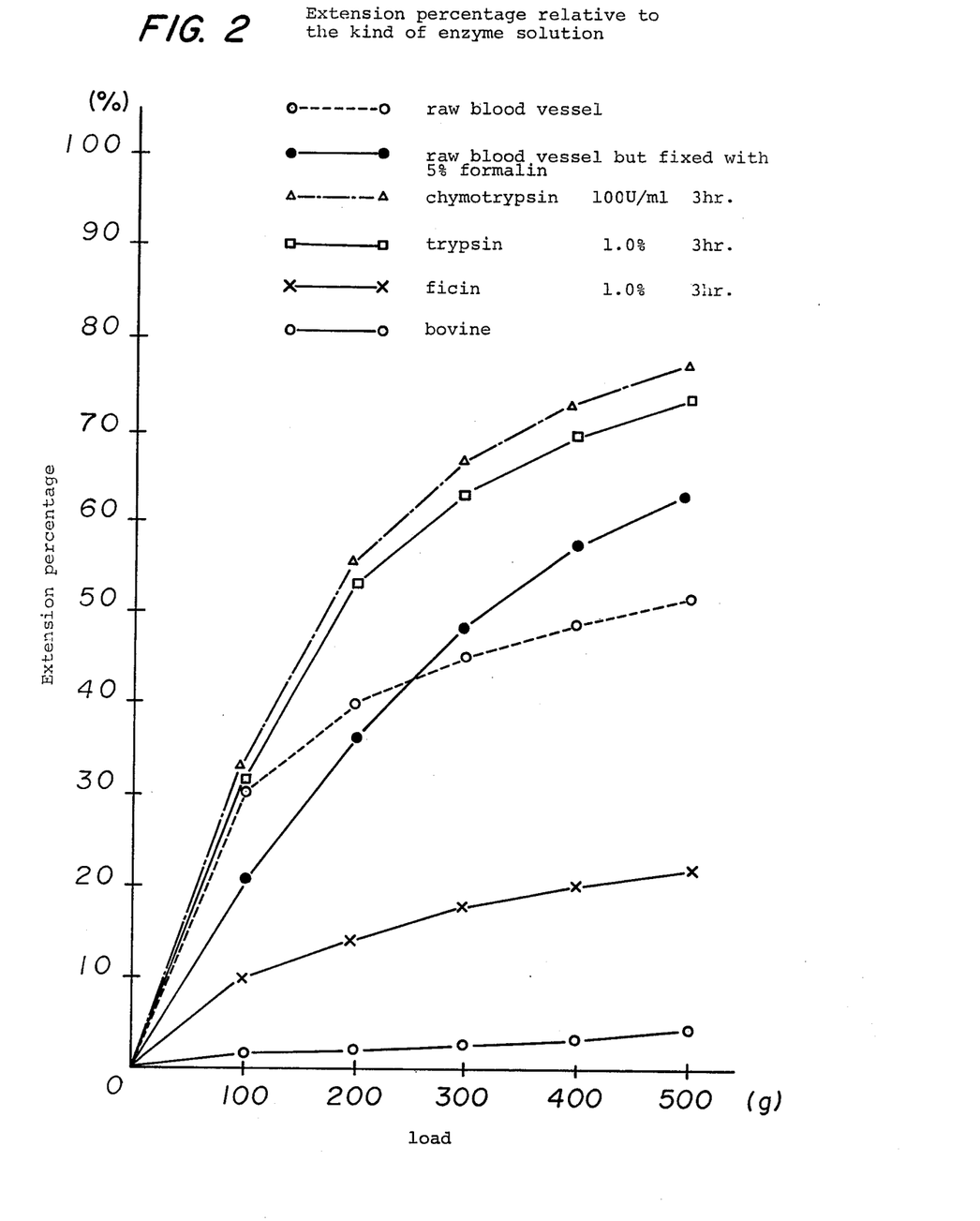
FIG. 2 is a graph illustrating the comparative test data between the extensibilities of a substitute blood vessel according to the present invention, a raw blood vessel and a collagen tube obtained from a bovine blood vessel.
Figure 3:
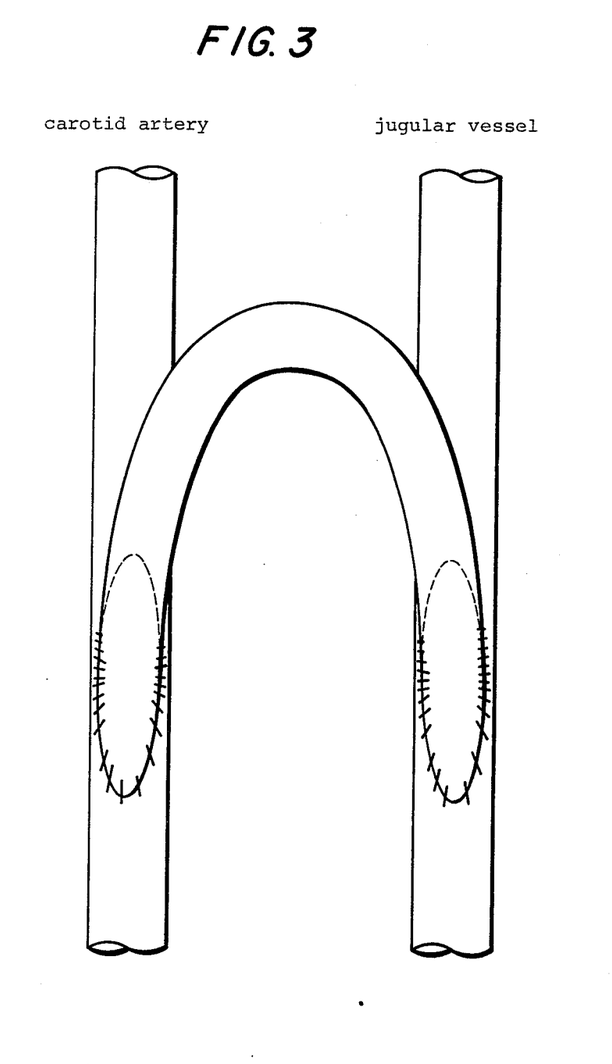
FIG. 3 is an explanatory view of an implantation test of a substitute blood vessel.

Products as specimens were obtained by the treatment with the enzyme solutions of the abovementioned concentrations according to the process of Example (but all with 3 hour digesting time). Extention test was performed on the products, the result of which is shown in FIG. 2.

From this drawing, it is understood that the products treated with chymotrypsin (100 U/ml) and with trypsin (1.0%) respectively showed extremely excellent elasticity. In contrast, those treated with ficin were regarded as unsuitable for a substitute blood vessel.

HISTOLOGICAL TEST

Sections of the blood vessel of Example 1 (100 U/ml chymotrypsin) and another section as reference (treated with ficin) were washed with physiological salt solution, immersed and fixed in 10% neutral formalin. After freed from paraffin, the histological preparations were subject to hematoxylin-eosin dying and orcein dying, and disappearance of the elastic fibers were mainly observed.

TREATMENT WITH CHYMOTRIPSIN (EXAMPLE 1)

Specimens treated with chymotripsin for 1, 2 and 3 hours respectively retained elastic fibers as sufficiently as before the treatment. In 4 hour-treated specimens, some cracks were observed in elastic fibers inside the media, but this was only partly and had substantially no influence. In case of 5 hour-treatment, disappearance and crack of fibers were observed a quarter inside the media, while the inner elastic wall was well retained, however.

This means that treatment with chymotripsin up to 4 hours has no influence upon the elastic fibers.

TREATMENT WITH FICIN (REFERENCE)

After 1 hour-treatment with ficin, the inside and outside fibers of the media were partially disappeared, and some pieces of the fiber were observed. However, the central portion of the media was as well retained as before the treatment. After 2 hour-treatment, though similar range of fibers were retained to the case of 1 hour-treatment, the number of the elastic fibers showed a decreasing tendency. After 3 and 4 hour-treatments, no perfect elastic fiber was observed at all, with a small number of cracked fibers present. Further, elastic fibers completely disappeared after 5 hour-treatment with ficin.

It becomes apparent from the above that elastic fibers are digested gradually from the outside and inside of the media with the lapse of the treating time.

By examining Examples and tests above, the digesting treatment in the process according to the present invention can be easily controlled, i.e. substantial retention of collagenous and elastic fibers and at the same time substantial removal by digestion of other blood vessel tissue constituents can be easily achieved.

In contrast, it will be easily appreciated that in case of treatment with ficin, elastic fibers are rapidly decomposed, thus making difficult the control of the digesting treatment.

In the treatment with animal proteolytic enzymes, the enzymes act moderately upon elastic fibers to remarkably facilitate the control of the digesting treatment.

In addition, as well known, if there are retained tissue constituents other than the said two constituents forming a substitute blood vessel according to the present invention, it is disadvantageous in respects of antigenicity, degeneration of the blood vessel in the course of continued use.

ANTIGENICITY TEST

Eluate of four kinds of substitute blood vessels obtained by different digesting and fixing treatments were examined for antigenicity.

10 – 15cm long substitute blood vessels were cut into thin pieces and freeze-dried in a conventional manner. 10ml physiological salt solution was added to 1g of the original blood vessel and Ultra Sonic Osc. was operated thereon for 15 minutes. Then the substantial constituents were eluted with Teflon Homogenizer as much as possible. After centrifuging the eluate, a part of the supernatant was taken and the equal volume of complete adjuvant by Freund was added thereto to form an immunogen in water-in-oil state. 0.1ml of the immunogen was hypodermically inoculated into the abdominal region of each of two guinea pigs per one specimen five times on a basis of once every other day. Three weeks after the last inoculation, 3ml of the remaining supernatant was intravenously injected into a saphena of a hind leg to observe the presence or absence of anaphylactic shock occurence.

On the other hand, sections of fresh pig carotid artery freed from fat and connective tissue on the adventitia were only washed with physiological salt solution, and then subject to the similar eluting treatment. Using the eluate, immunization was similarly performed to provide the references.

The results are shown in Table 5 below. Within the conditions of the abovementioned experiment and using water-soluble component eluted from the substitute blood vessel as immunogen, no occurence of anaphylactic shock was observed. All of the guinea pigs immunized with eluate from the raw blood vessel showed typical anaphylactic shock e.g. difficulty in breathing, clonus and the like and died on the provoking injection of the said eluate.

When the dead guinea pigs were anatomized and examined, it was observed that the lungs were expanded around the whole thoracic cavities and that the peritoneum and digestive canals were congested.

Table 5

| substitute blood vessel enzyme | treating temp. & time | fixing solution & time | anaphylactic shock |
|---|---|---|---|
| heparin 10U/ml | 37° C, 3 hours | | — |
| heparin 10U/ml urokinase 12IU/ml chymotripsin 10U/ml | " | | — |
| " | " | 5% formalin 2 weeks | — |
| " | " | 3% gultaric aldehyde 2 weeks | — |
| raw blood vessel | | | + + |

IMPLANTATION TEST

Substitute blood vessels thus obtained, other artificial blood vessels and raw blood vessels were anatomosed with the complete carotid artery and jugular vessel of twenty dogs to provide bypasses, and the progress was observed. After implantation, the dogs were sacrificed with the lapse of time to examine change of the implanted parts, anastomised parts, and inside and outside of the implanted blood vessels in respect of appearance and histology, but five dogs of them are now being bred.

Example of substitute blood vessel implantation (1):

A 15kg weight of adult mongrel dog was subject to general anesthesia by intravenous injection of pentobarbital Na (similar anesthesia was performed in the following Examples), and the skin of the right cervical region was cut to expose the whole of the right carotid artery and jugular vessel. Blood flow was stopped with two Bulldog forceps disposed at 5cm spaced two points of the blood vessel, and a small longitudinal cut was provided in each of the blood vessels. Two ends of each of said cuts were seamed with the ends of a U-shaped substitute blood vessel (obtained similarly to Example 1 by digesting with 10 U/ml chymotrypsin, and two weeks' fixing treatment with 5% formalin) with 5-0 suture (nonabsorable, U.S.P.), and the periphery was continuously seamed to achieve the anastomosis of the substitute blood vessel with the carotid artery and jugular vessel. The forceps were then removed and blood flow re-established. (In the following Examples, the anastomosis between a substitute blood vessel, carotid artery and jugular vessel were performed in a similar manner.) At this stage, slight bleeding from the anastomosed parts, but it was arrested by slightly pressing with sterile gauze.

The anastomosed substitute blood vessel was put inside the skin, and the cut section was seamed together, thus completing the implanting operation.

This dog after operation did not show any remarkable change of its weight, motion, ingestion amount and the like and was normally bred, and the blood flow sound was certainly heard with a stethoscope.

At 71 days after operation, a indwelling needle was inserted into the said substitute blood vessel and blood perfusion test was performed using a blood perfusing apparatus for children. As the result, blood was perfused outside the body without anything unusual. After this test, when the dog was sacrificed and the area of the substitute blood vessel implantation was taken out and observed with naked eyes, no abnormality was observed.

Implantation test (2)

A 8.2 kg weight of adult mongrel dog was subject to anesthesia and the skin of the right and left cervical regions was cut. A 10 cm substitute blood vessel (obtained similarly to Example 1 by digesting with 100 U/ml chymotrypsin, and two weeks' fixing with 5% formalin) anastomosed with the whole of the left jugular vessel was passed under the partly separated skin of the laryngeal region, taken out of a cut provided in the right jugular region, and anastomosed with the whole of the right carotid artery, then the cut sections were seamed together. Thereafter the dog did not show any abnormal act with blood flow sound confirmed, and is being bred well now i.e. 80 days after the operation.

Example of an artificial blood vessel implantation:

A 9 kg weight of adult mongrel dog was subject to anesthesia and a 4 mm-diametered Teflon artificial blood vessel was anastomosed with the whole of the right jugular vessel and left carotid artery to provide a bypass similarly to the case of the implantation test 2 above. On removing forceps to re-establish the blood flow, blood oozed up throughout substantially the whole surface of the artificial blood vessel from the artery side to the jugular vessel side. 10 minutes after pressing the artificial blood vessel with sterile gauze, the blood leakage stopped substantially, and thus the cut sections were seamed together. The next day, the implantation area on the artery side was found to have expanded, and further blood flow sound could not be heard. After 5 days, blood was examined to find that the number of red cells was reduced from 5900 thousands which is the number before the operation to 1440 thousands as well as that the hematocrit value (12.8%) and the blood platelet (10.2%) remarkably show an anemia. When the dog was therefore sacrificed and the implanted part was cut out, the inside was found to be filled with coagulated blood. The implanted artificial blood vessel with the artery and the jugular vessel was taken out and observed with naked eye. As the result, the anastomosed part on the artery vessel side was found to be open through 2 × 4 mm, and it proved that the expansion was not due to continuous blood leakage from the artificial blood vessel but due to bleeding from the cut caused by unsatisfactory seaming. Thrombus was attached to substantially the whole of the inside of the artificial blood vessel.

Example of raw blood vessel implantation:

In this experiment, according to the present preparing process, a pig carotid artery carried home in a physiological salt solution containing 10,000 U/l heparin sodium and then freed of fat and connective tissue.

A 14 kg weight of adult mongrel dog was subject to anesthesia, and an operation was performed so that a raw blood vessel was anastomosed to the whole of the left carotid artery and right jugular vessel in the similar manner as abovementioned. This dog was kept well, and the blood flow sound could be surely heard, but the implanted part was suddenly expanded on 29th day after the operation. The next day, the dog was sacrificed and the implanted part was cut out to find that coagulated blood was filled, and the implanted blood vessel was broken at the parts of anastomosis with the artery and jugular vessel and at a middle part, with 3 - 5 mm diametered breaks at other positions.

From the abovementioned clinical and physiological experiments, it can be understood that a substitute blood vessel according to the present invention has extremely advantageous properties from the medical viewpoint, too.

What is claimed is:

1. A process for preparing a heterograft substitute blood vessel comprising digesting a properly pretreated pig blood vessel with a digesting solution containing an animal proteolytic enzyme so as to retain collagenous and elastic fiber constituents substantially in the original state and substantially remove away other tissue constituents of said blood vessel than said two kinds of constituents, and then fixing the resulting digested blood vessel into a desired shape with a liquid fixing agent.

2. A process as claimed in claim 1, in which said animal proteolytic enzyme is at least one selected from a group consisting of pepsin, trypsin and chymotrypsin.

3. A process as claimed in claim 1, in which said pig blood vessel is a raw or a protein denaturated blood vessel obtained by freeze-preservation.

4. A process as claimed in claim 1, in which said liquid fixing agent comprises 5 - 10% formalin solution or 2 - 25% glutaric aldehyde solution.

5. A process as claimed in claim 1, in which said digesting solution is a mixed buffer solution containing an animal proteolytic enzyme, a thrombus dissolving agent and an anticoagulating agent.

6. A process as claimed in claim 1, in which said digesting treatment is performed at pH 1.8 - 9.0, at 30° - 40° C for 2 - 8 hours.

7. A process as claimed in claim 1, in which said digesting treatment is controlled so that extension percentage of the resulting heterograft substitute blood vessel is more than 40% under 200 g load and its tensile strength more than 1.0 kg.

8. A process as claimed in claim 1, in which said digesting treatment comprises digesting a raw pig blood vessel with a digesting solution containing about 100 U/ml chymotrypsin at pH 6 - 8 and at 30° - 40° C for 3 - 8 hours.

9. A process as claimed in claim 1, in which said digesting treatment comprises digesting a raw pig blood vessel with a digesting solution containing about 1% trypsin at pH 6 - 8 and at 30° - 40° C for 3 - 8 hours.

10. A heterograft substitute blood vessel obtained according to the process as claimed in claim 1 and having more than 40% extension percentage under 200 g load and more that 1.0 kg tensile strength.

* * * * *